(12) United States Patent
McGrath

(10) Patent No.: US 7,053,046 B2
(45) Date of Patent: May 30, 2006

(54) PEPTIDE ACTIVATORS OF VEGF

(76) Inventor: Kevin McGrath, 335 Hermitage Trail, Alpharetta, GA (US) 30004

( * ) Notice: Subject to any disclaimer, the term of this patent is extended or adjusted under 35 U.S.C. 154(b) by 478 days.

(21) Appl. No.: 10/032,361

(22) Filed: Dec. 21, 2001

(65) Prior Publication Data

US 2004/0214777 A1 Oct. 28, 2004

(51) Int. Cl.
*A61K 38/16* (2006.01)
*C12N 7/00* (2006.01)

(52) U.S. Cl. .......................... 514/8; 530/300; 530/402; 435/440

(58) Field of Classification Search ................ 514/8; 530/300, 402; 435/440
See application file for complete search history.

(56) References Cited

U.S. PATENT DOCUMENTS 6,124,131 A * 9/2000 Semenza .................... 435/325
6,566,088 B1 * 5/2003 McKnight et al. ............ 435/24

FOREIGN PATENT DOCUMENTS

GB WO 0069908 * 11/2000

OTHER PUBLICATIONS

Jaakkola P. et al. (2001) Targeting of HIF-alpha to the von Hippel-Lindau ubiquitylation complex by O23-regulated prolyl hydroxylation. Science. vol. 292, pp. 468-472.*
Jones, A. et al. (2001) Relation of vascular endothelial growth factor production to expression and regulation of hypoxia-inducible factor-1 alpha and hypoxia-inducible factor-2 alpha in human bladder tumors and cell lines. Clin Cancer Res. 7, 1263-1272.*
Yu, F. et al. (2001) HIF-1alpha binding to VHL is regulated by stimulus-sensitive proline hydroxylation. Proc Natl Acad Sci U S A. vol. 98, pp. 9630-9635.*
Bruick, R. et al. (2001) conserved family of prolyl-4-hydroxylases that modify HIF. Science. vol. 294, pp. 1337-1340.*
Cockman, M.,et al. ,"Hyposix Inducible Factor-alpha Binding and Ubiqitylation by the von Hippel-Lindau Tumor Supressor Protein", *The Journal of Biological Chemistry*, 275(33), (2000),pp. 25733-25741.
Der, S.,et al. ,"Identification of genes differentially regulated by interferon alpha, B, or y using oligonucleotide arrays", *Proc. Natl. Acad, Sci. USA*, 95, (1998), pp. 15623-15628.
Gradin, K.,et al. ,"Repression of Dioxin Signal Transduction in Fibroblasts", *The Journal of Biological Chemistry*, 274(19), (1999),pp. 13511-13518.
Hossain, M.,et al. ,"Induction of Vascular Endothelial Growth Factor in Human Astrocytes by Lead", *the Journal of Biological Chemistry*, 274(36), (2000),pp. 27874-27882.
Huang, L.,et al. ,"Regulation of hypoxia-inducible factor 1alpha is mediated by an O2-dependent degradation domain via the ubiquitin-proteasome pathway", *Proc. Natl. Acad. Sci. USA. 95*, (1998),pp. 7987-7992.
Iyer, N.,et al. ,"Celluar and developmental control of O2 homeostasis by hypoxia-inducible factor 1alpha", *Genes & Development*, 12, (1998),pp. 149-162.
Kamura, T.,et al. ,"Activation of HIF1alpha ubiquitination by a reconstituted von Hippel-Lindau (VHL) tumor suppressor complex", *PNAS*, 97(19), (2000),pp. 10430-10435.
Mathupala, S.,et al. ,"Glucose Catabolism in Cancer Cells: Indentification and Charcterization of A Marked Activation Response of The Type II Hexokinase Gene to Hypoxic Condition", *The American Society for Biochemistry and Molecular Biology, Inc.*,pp. 1-24.
Scheid, A.,et al. ,"Hypoxia-regulated gene expression in fetal wound regeneration and adult wound repair", *Pediatr. Surg. Int.*, 16, (2000),pp. 232-236.

(Continued)

*Primary Examiner*—Jon Weber
*Assistant Examiner*—Samuel Wei Liu
(74) *Attorney, Agent, or Firm*—Schwegman, Lundberg, Woessner & Kluth, P.A.

(57) ABSTRACT

The invention provides peptide inhibitors that inhibit ubiquitination of hypoxia inducible factor 1 alpha (HIP 1-α) and thereby activate transcription of erythropoietin (EPO), vascular endothelial growth factor (VEGF), and certain glycolytic enzymes. The invention further provides formulations containing the present peptides and methods of using the present peptides for therapeutic purposes. Such therapeutic purposes include stimulating angiogenesis in injured tissues such as chronic wounds, heart tissues injured by ischemia or heart attack, and neural tissues injured by stroke.

5 Claims, 9 Drawing Sheets

OTHER PUBLICATIONS

Figure 1:
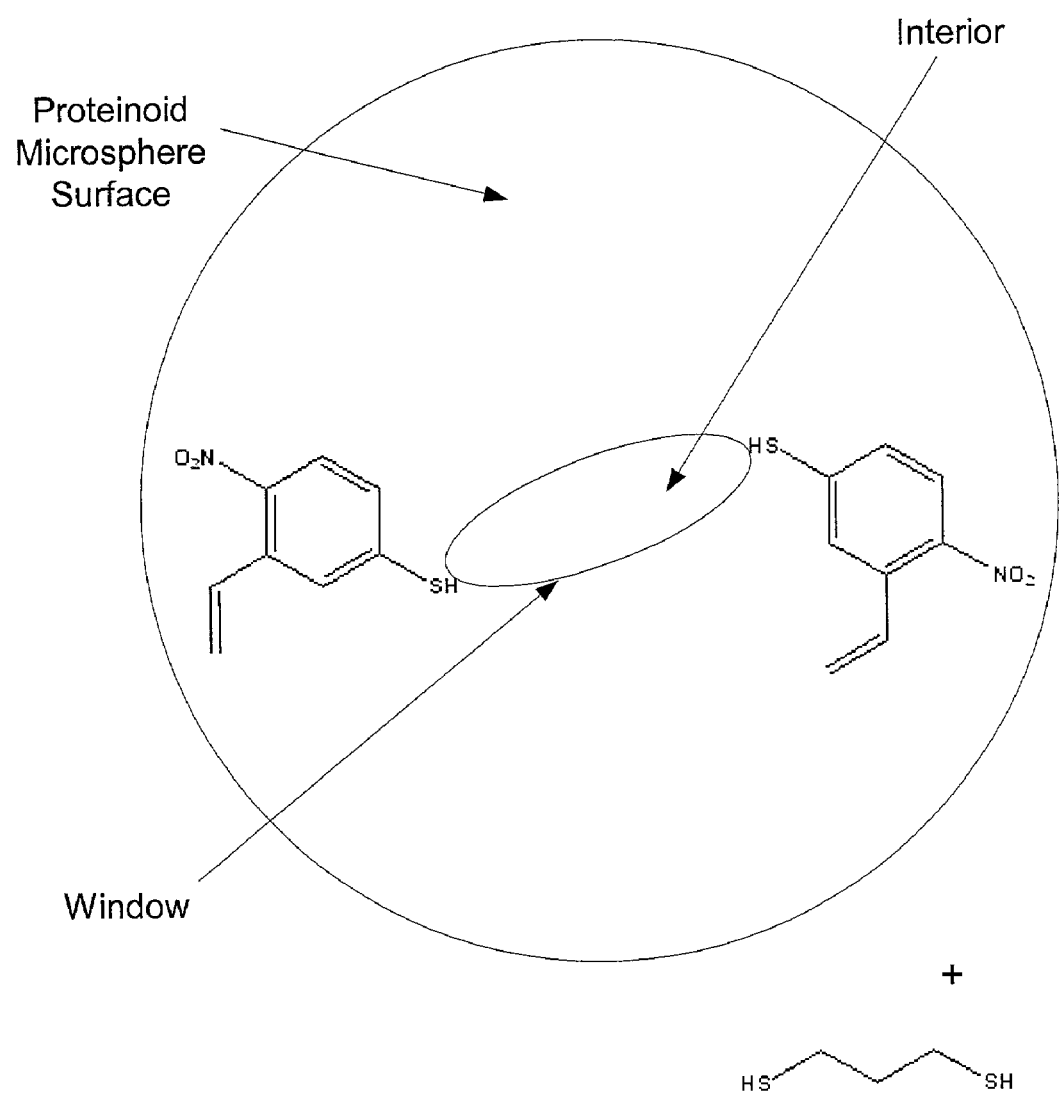
Figure 2:
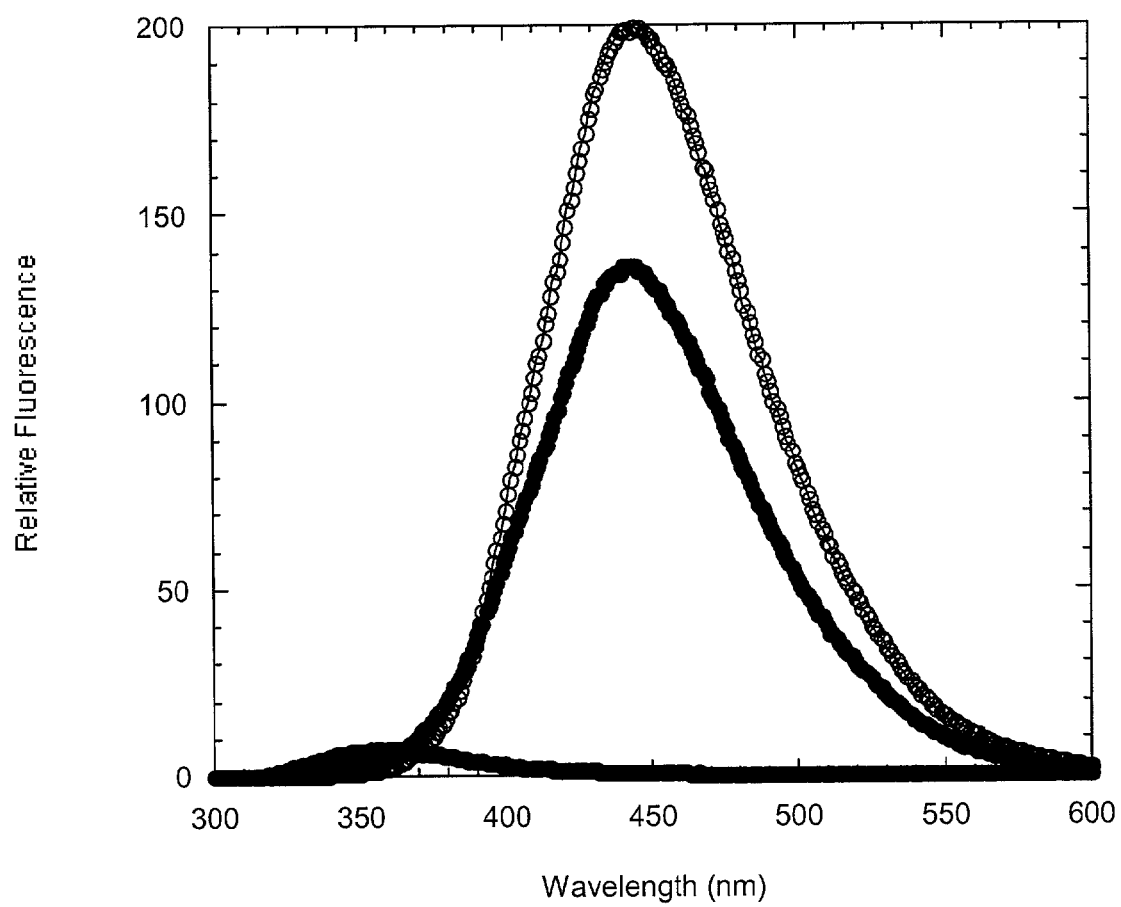
Figure 3:
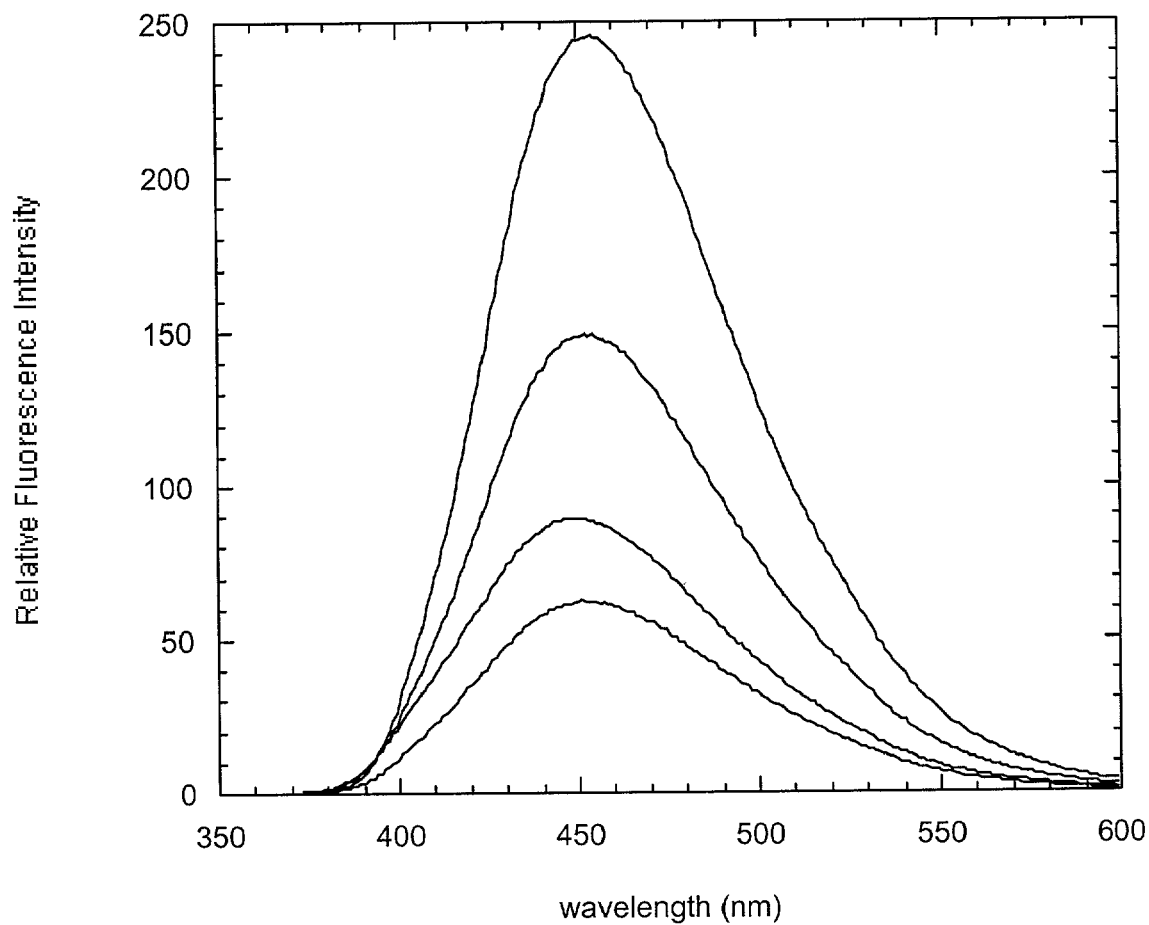
Figure 4:
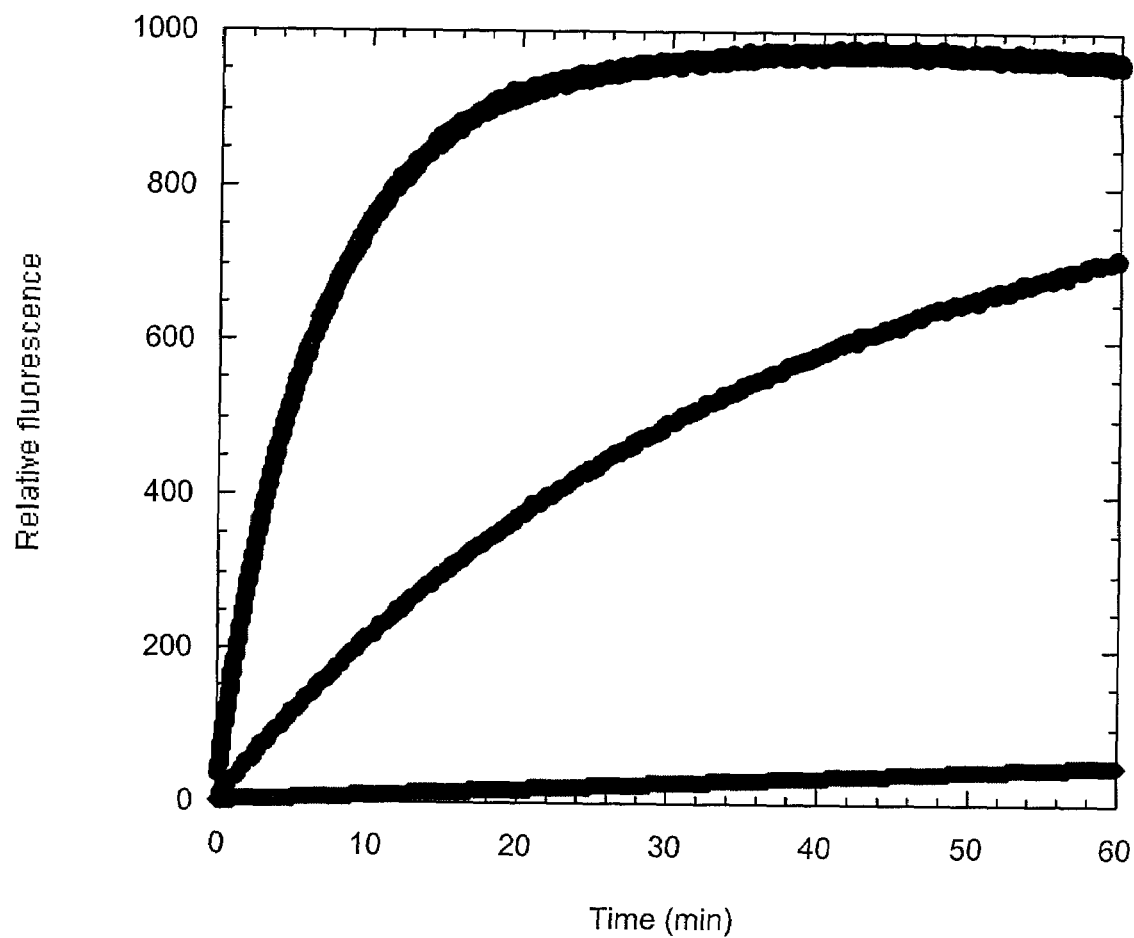
Figure 5:
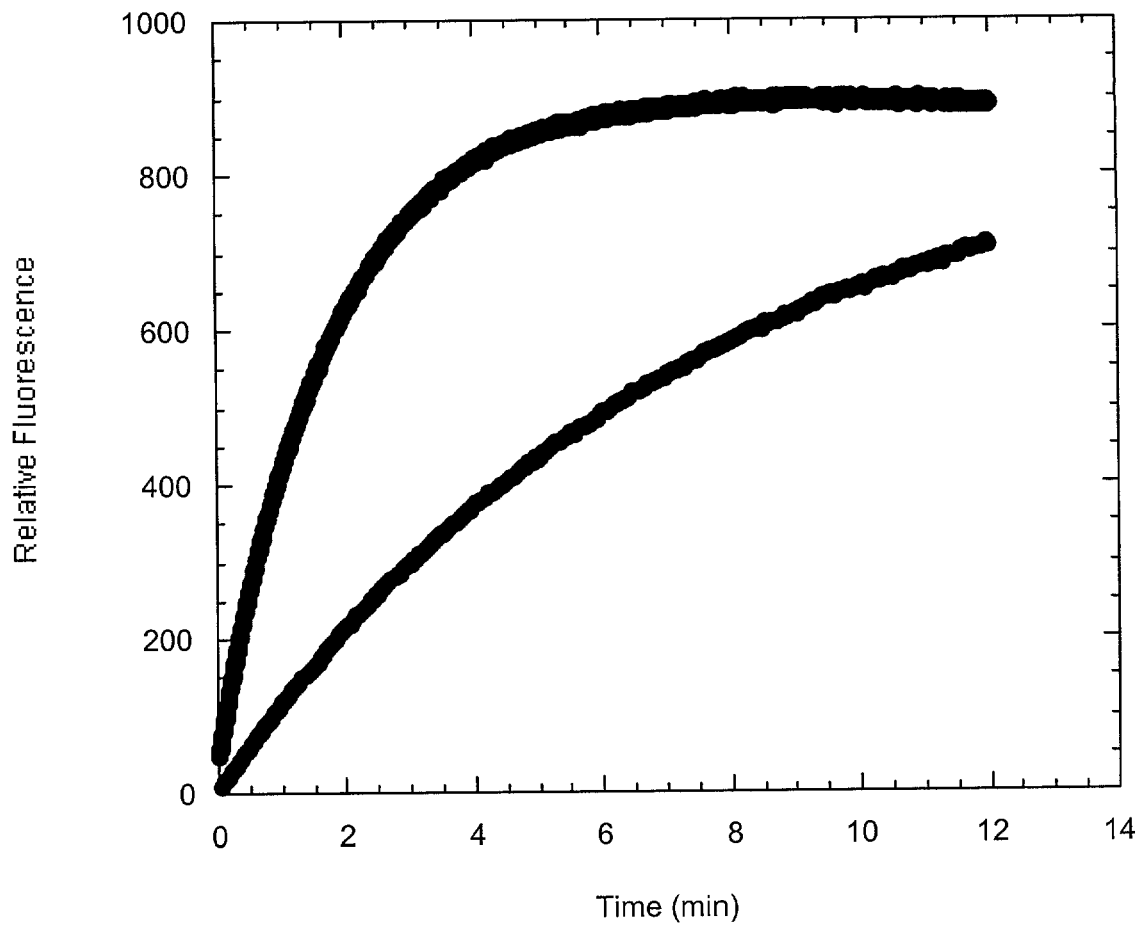
Figure 6:
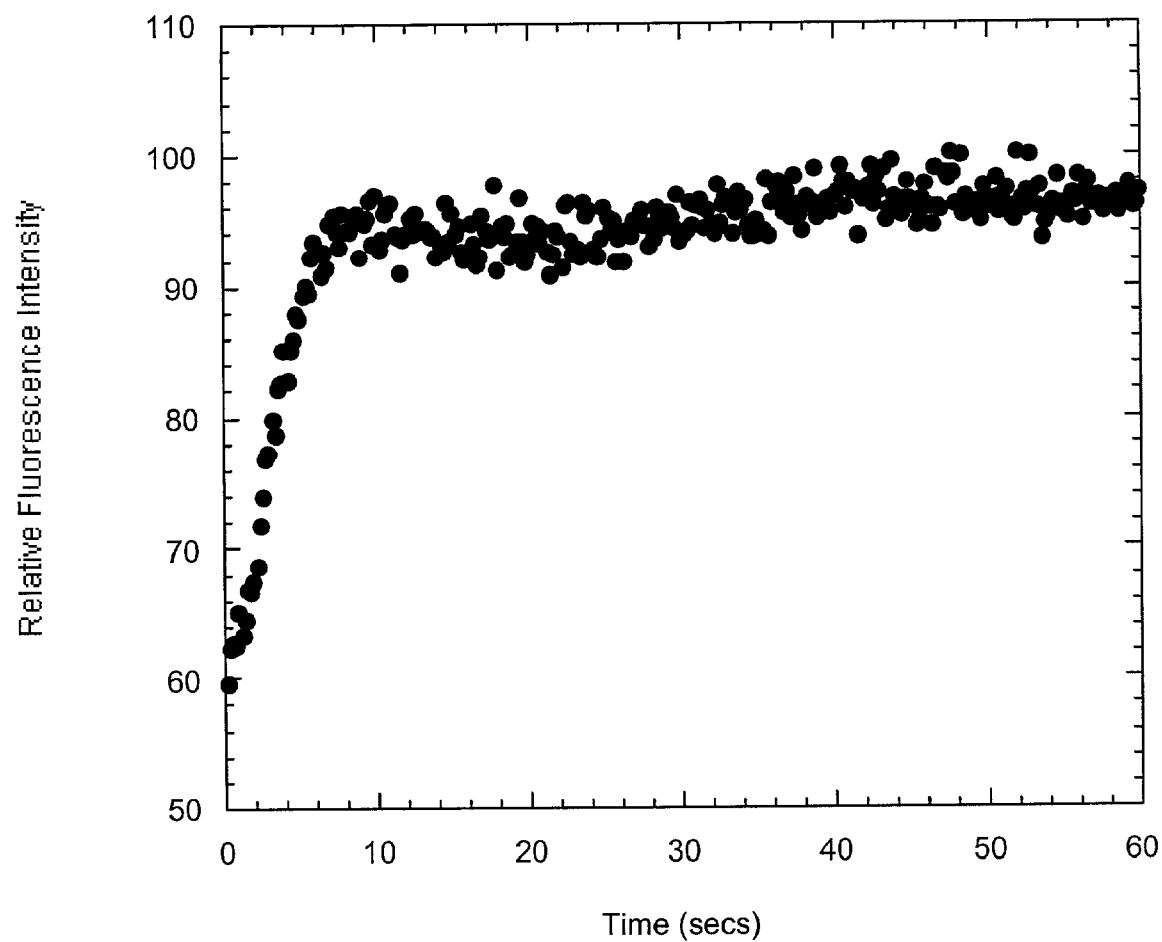
Figure 7:
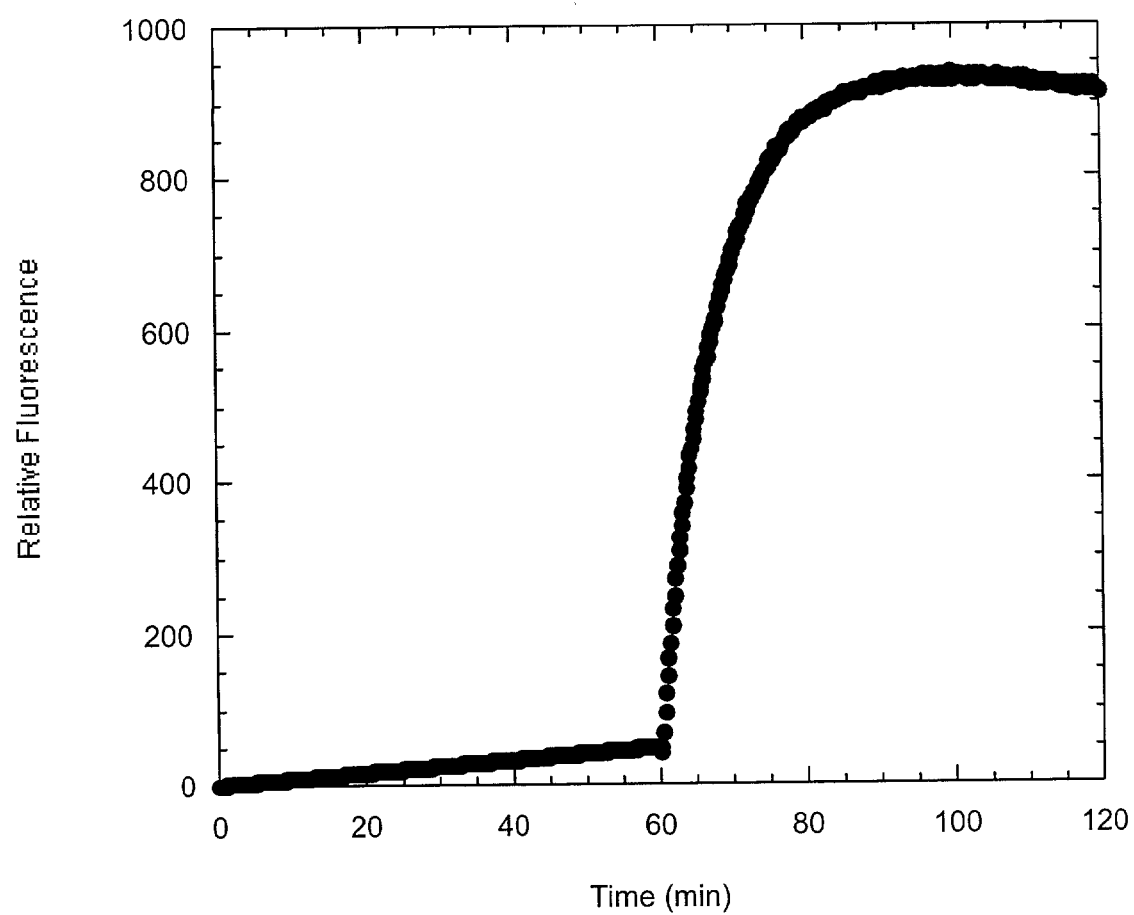
Figure 8:
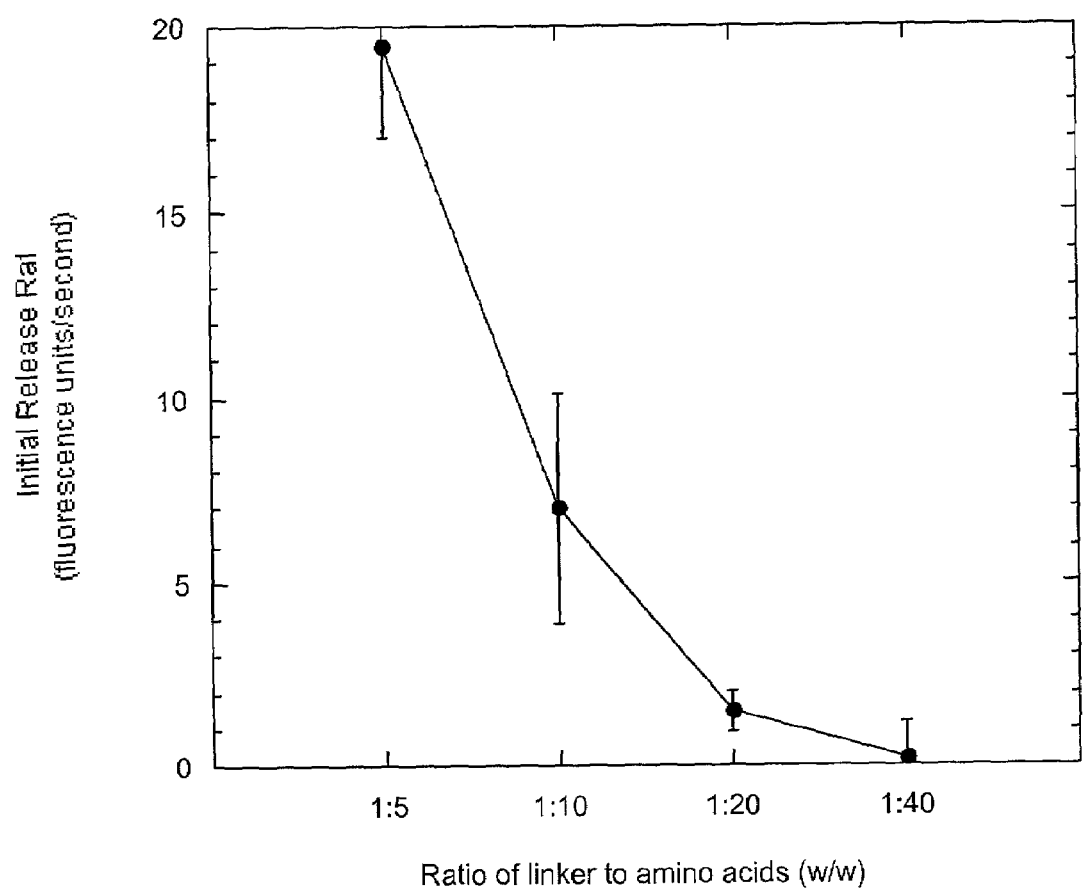
Figure 9:
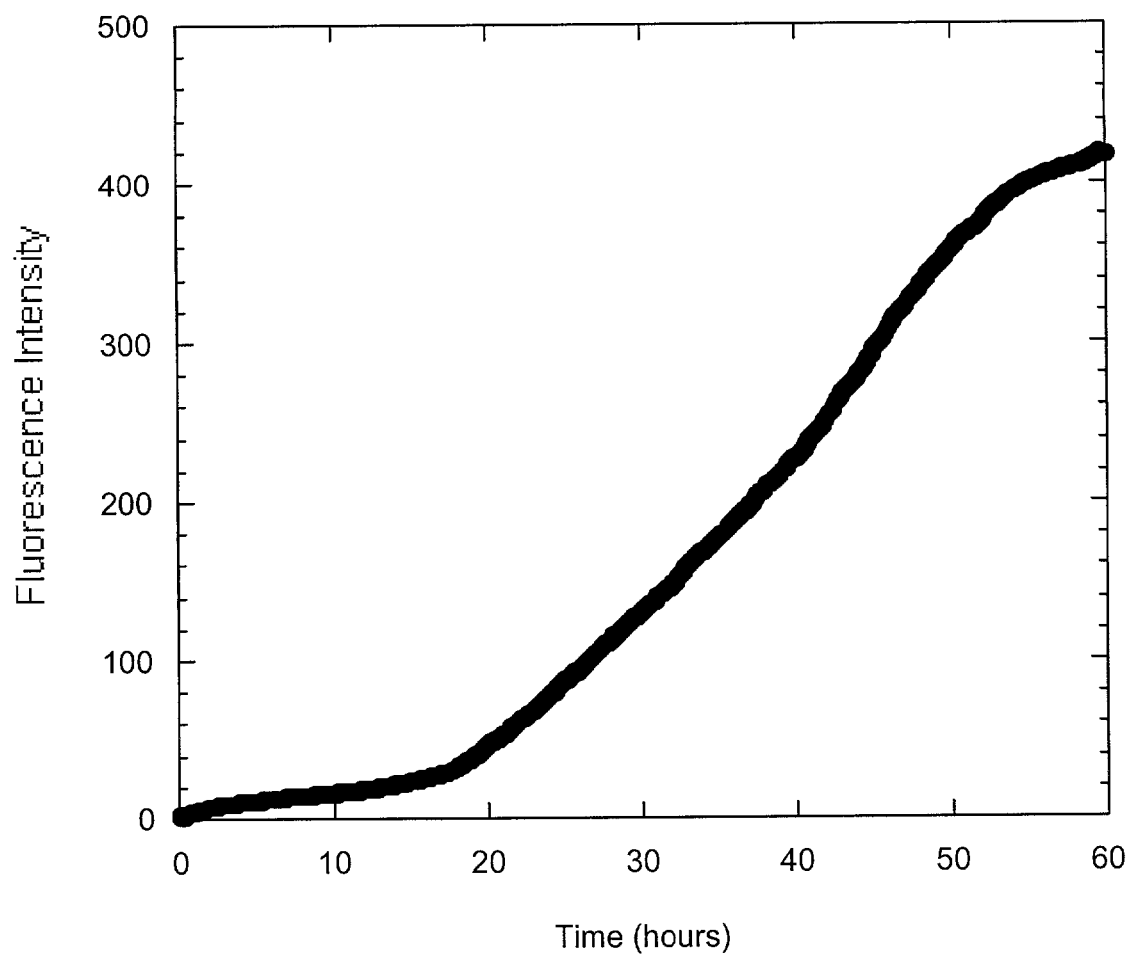

Semenza, G., "HIF-1: mediator of physiological and pathophysiological to hypoxia", *J. Appl. Physiol.*, 88, (2000), pp. 1474-1480.

Sutter, C., et al., "Hypoxia-inducible factor 1alpha protein expression in controlled by oxygen-regulated ubiquitination that is disrupted by deletions and missense mutations", *PNAS*, 97(9), (2000), pp. 4748-4753.

Takahashi, Y., et al., "Hypoxic Induction of Prolyl 4-Hydroxylase alpha(I) in cultured cells", *The Journal of Biological Chemistry*, 275(19), (2000), pp. 14139-14146.

Tanimoto, K., et al., "Mechanism of regulation of the hypoxia-inducible factor-1alpha by the von Hippel-Lindau tumor suppressor protein", *The EMBO Journal*, 19(16), (2000), pp. 4298-4309.

Wenger, R., "Review—Mammalian Oxygen Sensing, Signalling and Gene Regulation", *The Journal of Experimental Biology*, 203, (2000), pp. 1253-1263.

Yu, F., et al., "HIF-1alpha binding to VHL is regulated by stimulus-sensitive proline hydroxylation", *PNAS*, 98(17), (2001), pp. 9630-9635.

Zhong, H., et al., "Overexpression of Hypoxia-inducible Factor 1alpha in Common Human Cancers and Their Metastases", *Cancer Research*, 59, (1999), pp. 5830-5835.

Gudmundsson, G. H., et al., "Structure of the Gene for Porcine Peptide Antibiotic PR-39, a Cathelin Gene Family Member: Comparative Mapping of the Locus for the Human Peptide Antibiotic Fall-39", *Proc. Natl. Acad. Sci. USA*, 92, (1995), 7085-7089.

Krek, W., "VHL Takes HIF's Breath Away", *Nature Cell Biology*, 2, (2000) E1-E3.

Li, J., et al., "PR39, a Peptide Regulator of Angiogenesis", *Nature Medicine*, 6, (2000), 49-55.

Lisztwan, J., et al., "The Von Hippel-Lindau Tumor Suppressor Protein is a Component of an E3 Ubiquitin-Protein Ligase Activity", *Gene and Development*, 13, (1999), 1822-1833.

Ratliffe, P. J., et al., "Oxygen Sensing, Hypoxia-Inducible Factor-1 and the Regulation of Mammalian Gene Expression", *The Journal of Experimental Biology*, 201, (1998), 1153-1162.

* cited by examiner

SEQUENCE LISTING

<160> NUMBER OF SEQ ID NOS: 7

<210> SEQ ID NO 1
<211> LENGTH: 826
<212> TYPE: PRT
<213> ORGANISM: Homo sapiens

<400> SEQUENCE: 1

```
Met Glu Gly Ala Gly Gly Ala Asn Asp Lys Lys Ile Ser Ser Glu
 1               5                  10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
```

```
                355                 360                 365
Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780
```

-continued

```
Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 2
<211> LENGTH: 735
<212> TYPE: PRT
<213> ORGANISM: Homo sapiens

<400> SEQUENCE: 2

Met Glu Gly Ala Gly Gly Ala Asn Asp Lys Lys Lys Ile Ser Ser Glu
  1               5                  10                  15

Arg Arg Lys Glu Lys Ser Arg Asp Ala Ala Arg Ser Arg Arg Ser Lys
                 20                  25                  30

Glu Ser Glu Val Phe Tyr Glu Leu Ala His Gln Leu Pro Leu Pro His
             35                  40                  45

Asn Val Ser Ser His Leu Asp Lys Ala Ser Val Met Arg Leu Thr Ile
         50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
```

```
                      325                 330                 335
Cys Val Asn Tyr Val Ser Gly Ile Ile Gln His Asp Leu Ile Phe
                340                 345                 350
Ser Leu Gln Gln Thr Glu Cys Val Leu Lys Pro Val Glu Ser Ser Asp
            355                 360                 365
Met Lys Met Thr Gln Leu Phe Thr Lys Val Glu Ser Glu Asp Thr Ser
        370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
                420                 425                 430
Asp Val Met Leu Pro Ser Pro Asn Glu Lys Leu Gln Asn Ile Asn Leu
            435                 440                 445
Ala Met Ser Pro Leu Pro Thr Ala Glu Thr Pro Lys Pro Leu Arg Ser
        450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
Pro Asn Ser Pro Ser Glu Tyr Cys Phe Tyr Val Asp Ser Asp Met Val
        515                 520                 525
Asn Glu Phe Lys Leu Glu Leu Val Glu Lys Leu Phe Ala Glu Asp Thr
        530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
            595                 600                 605
Glu Pro Thr Ala Asn Ala Thr Thr Thr Thr Ala Thr Thr Asp Glu Leu
        610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
                660                 665                 670
Gly Lys Gly Val Ile Glu Gln Thr Glu Lys Ser His Pro Arg Ser Pro
            675                 680                 685
Asn Val Leu Ser Val Ala Leu Ser Gln Arg Thr Thr Val Pro Glu Glu
        690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Ile
                725                 730                 735

<210> SEQ ID NO 3
```

<211> LENGTH: 789
<212> TYPE: PRT
<213> ORGANISM: Homo sapiens

<400> SEQUENCE: 3

```
Met Ala Ala Thr Thr Ala Asn Pro Glu Met Thr Ser Asp Val Pro Ser
 1               5                  10                  15

Leu Gly Pro Ala Ile Ala Ser Gly Asn Ser Gly Pro Gly Ile Gln Gly
            20                  25                  30

Gly Gly Ala Ile Val Gln Arg Ala Ile Lys Arg Arg Pro Gly Leu Asp
        35                  40                  45

Phe Asp Asp Gly Glu Gly Asn Ser Lys Phe Leu Arg Cys Asp Asp
50                  55                  60

Asp Gln Met Ser Asn Asp Lys Glu Arg Phe Ala Arg Ser Asp Asp Glu
65                  70                  75                  80

Gln Ser Ser Ala Asp Lys Glu Arg Leu Ala Arg Glu Asn His Ser Glu
                85                  90                  95

Ile Glu Arg Arg Arg Arg Asn Lys Met Thr Ala Tyr Ile Thr Glu Leu
            100                 105                 110

Ser Asp Met Val Pro Thr Cys Ser Ala Leu Ala Arg Lys Pro Asp Lys
        115                 120                 125

Leu Thr Ile Leu Arg Met Ala Val Ser His Met Lys Ser Leu Arg Gly
130                 135                 140

Thr Gly Asn Thr Ser Thr Asp Gly Ser Tyr Lys Pro Ser Phe Leu Thr
145                 150                 155                 160

Asp Gln Glu Leu Lys His Leu Ile Leu Glu Ala Ala Asp Gly Phe Leu
                165                 170                 175

Phe Ile Val Ser Cys Glu Thr Gly Arg Val Val Tyr Val Ser Asp Ser
            180                 185                 190

Val Thr Pro Val Leu Asn Gln Pro Gln Ser Glu Trp Phe Gly Ser Thr
        195                 200                 205

Leu Tyr Asp Gln Val His Pro Asp Asp Val Asp Lys Leu Arg Glu Gln
210                 215                 220

Leu Ser Thr Ser Glu Asn Ala Leu Thr Gly Arg Ile Leu Asp Leu Lys
225                 230                 235                 240

Thr Gly Thr Val Lys Lys Glu Gly Gln Gln Ser Ser Met Arg Met Cys
                245                 250                 255

Met Gly Ser Arg Arg Ser Phe Ile Cys Arg Met Arg Cys Gly Ser Ser
            260                 265                 270

Ser Val Asp Pro Val Ser Val Asn Arg Leu Ser Phe Val Arg Asn Arg
        275                 280                 285

Cys Arg Asn Gly Leu Gly Ser Val Lys Asp Gly Glu Pro His Phe Val
290                 295                 300

Val Val His Cys Thr Gly Tyr Ile Lys Ala Trp Pro Pro Ala Gly Val
305                 310                 315                 320

Ser Leu Pro Asp Asp Pro Glu Ala Gly Gln Gly Ser Lys Phe Cys
                325                 330                 335

Leu Val Ala Ile Gly Arg Leu Gln Val Thr Ser Ser Pro Asn Cys Thr
            340                 345                 350

Asp Met Ser Asn Val Cys Gln Pro Thr Glu Phe Ile Ser Arg His Asn
        355                 360                 365

Ile Glu Gly Ile Phe Thr Phe Val Asp His Arg Cys Val Ala Thr Val
370                 375                 380

Gly Tyr Gln Pro Gln Glu Leu Leu Gly Lys Asn Ile Val Glu Phe Cys
```

-continued

```
             385                 390                 395                 400
His Pro Glu Asp Gln Gln Leu Leu Arg Asp Ser Phe Gln Gln Val Val
                405                 410                 415
Lys Leu Lys Gly Gln Val Leu Ser Val Met Phe Arg Phe Arg Ser Lys
            420                 425                 430
Asn Gln Glu Trp Leu Trp Met Arg Thr Ser Ser Phe Thr Phe Gln Asn
            435                 440                 445
Pro Tyr Ser Asp Glu Ile Glu Tyr Ile Ile Cys Thr Asn Thr Asn Val
            450                 455                 460
Lys Asn Ser Ser Gln Glu Pro Arg Pro Thr Leu Ser Asn Thr Ile Gln
465                 470                 475                 480
Arg Pro Gln Leu Gly Pro Thr Ala Asn Leu Pro Leu Glu Met Gly Ser
                485                 490                 495
Gly Gln Leu Ala Pro Arg Gln Gln Gln Gln Thr Glu Leu Asp Met
            500                 505                 510
Val Pro Gly Arg Asp Gly Leu Ala Ser Tyr Asn His Ser Gln Val Val
                515                 520                 525
Gln Pro Val Thr Thr Thr Gly Pro Glu His Ser Lys Pro Leu Glu Lys
            530                 535                 540
Ser Asp Gly Leu Phe Ala Gln Asp Arg Asp Pro Arg Phe Ser Glu Ile
545                 550                 555                 560
Tyr His Asn Ile Asn Ala Asp Gln Ser Lys Gly Ile Ser Ser Ser Thr
                565                 570                 575
Val Pro Ala Thr Gln Gln Leu Phe Ser Gln Gly Asn Thr Phe Pro Pro
            580                 585                 590
Thr Pro Arg Pro Ala Glu Asn Phe Arg Asn Ser Gly Leu Ala Pro Pro
            595                 600                 605
Val Thr Ile Val Gln Pro Ser Ala Ser Ala Gly Gln Met Leu Ala Gln
            610                 615                 620
Ile Ser Arg His Ser Asn Pro Thr Gln Gly Ala Thr Pro Thr Trp Thr
625                 630                 635                 640
Pro Thr Thr Arg Ser Gly Phe Ser Ala Gln Gln Val Ala Thr Gln Ala
                645                 650                 655
Thr Ala Lys Thr Arg Thr Ser Gln Phe Gly Val Gly Ser Phe Gln Thr
            660                 665                 670
Pro Ser Ser Phe Ser Ser Met Ser Leu Pro Gly Ala Pro Thr Ala Ser
            675                 680                 685
Pro Gly Ala Ala Ala Tyr Pro Ser Leu Thr Asn Arg Gly Ser Asn Phe
            690                 695                 700
Ala Pro Glu Thr Gly Gln Thr Ala Gly Gln Phe Gln Thr Arg Thr Ala
705                 710                 715                 720
Glu Gly Val Gly Val Trp Pro Gln Trp Gln Gly Gln Pro His His
                725                 730                 735
Arg Ser Ser Ser Glu Gln His Val Gln Gln Pro Ala Gln Gln
            740                 745                 750
Pro Gly Gln Pro Glu Val Phe Gln Glu Met Leu Ser Met Leu Gly Asp
            755                 760                 765
Gln Ser Asn Ser Tyr Asn Asn Glu Glu Phe Pro Asp Leu Thr Met Phe
            770                 775                 780
Pro Pro Phe Ser Glu
785

<210> SEQ ID NO 4
```

```
<211> LENGTH: 8
<212> TYPE: PRT
<213> ORGANISM: Homo sapiens
<220> FEATURE:
<221> NAME/KEY: SITE
<222> LOCATION: 4
<223> OTHER INFORMATION: Xaa = Hydroxyproline

<400> SEQUENCE: 4

Met Leu Ala Xaa Thr Ile Pro Met
  1               5

<210> SEQ ID NO 5
<211> LENGTH: 19
<212> TYPE: PRT
<213> ORGANISM: Homo sapiens
<220> FEATURE:
<221> NAME/KEY: SITE
<222> LOCATION: 9
<223> OTHER INFORMATION: Xaa = Hydroxyproline

<400> SEQUENCE: 5

Asp Leu Asp Leu Glu Met Leu Ala Xaa Tyr Ile Pro Met Asp Asp
  1               5                  10                  15

Phe Gln Leu

<210> SEQ ID NO 6
<211> LENGTH: 11
<212> TYPE: PRT
<213> ORGANISM: Artificial Sequence
<220> FEATURE:
<223> OTHER INFORMATION: A peptide inhibitor

<400> SEQUENCE: 6

Tyr Gly Arg Lys Lys Arg Arg Gln Arg Arg Arg
  1               5                  10

<210> SEQ ID NO 7
<211> LENGTH: 30
<212> TYPE: PRT
<213> ORGANISM: Artificial Sequence
<220> FEATURE:
<223> OTHER INFORMATION: A peptide inhibitor
<221> NAME/KEY: SITE
<222> LOCATION: 20
<223> OTHER INFORMATION: Xaa = Hydroxyproline

<400> SEQUENCE: 7

Tyr Gly Arg Lys Lys Arg Arg Gln Arg Arg Arg Asp Leu Asp Leu Glu
  1               5                  10                  15

Met Leu Ala Xaa Tyr Ile Pro Met Asp Asp Asp Phe Gln Leu
                 20                  25                  30
```

PEPTIDE ACTIVATORS OF VEGF

FIELD OF THE INVENTION

The present invention relates to peptide inhibitors for preventing degradation of hypoxia-inducible factor 1 (HIF-1) and activating transcription of erythropoietin EPO, vascular endothelial growth factor (VEGF), and various glycolytic enzymes. The invention further relates to methods of using those peptide inhibitors for a variety of therapeutic purposes, including treatment of tissues injured by trauma, heart attack, stroke or by diminished blood flow.

BACKGROUND OF THE INVENTION

Mammals require molecular oxygen ($O_2$) for essential metabolic processes, including oxidative phosphorylation in which $O_2$ serves as electron acceptor during ATP formation. Hypoxia occurs when the demand for molecular oxygen exceeds supply. Hypoxia causes systemic, local, and intracellular homeostatic responses that include erythropoiesis by individuals who are anemic or at high altitude (Jelkmann (1992) Physiol. Rev. 72:449–489), neovascularization in ischemic myocardium (White et al. (1992) Circ. Res. 71:1490–1500), and glycolysis in cells cultured at reduced $O_2$ tension (Wolfle et al. (1983) Eur. J. Biochem. 135: 405–412). These adaptive responses either increase $O_2$ delivery or activate alternate metabolic pathways that do not require $O_2$.

Hypoxia-inducible gene products that participate in these responses include erythropoietin (EPO) (reviewed in Semenza (1994) Hematol. Oncol. Clinics N. Amer. 8:863–884), vascular endothelial growth factor (Shweiki et al. (1992) Nature 359:843–845; Banai et al. (1994) Cardiovasc. Res. 28:1176–1179; Goldberg & Schneider (1994) J. Biol. Chem. 269:4355–4359), and glycolytic enzymes (Firth et al. (1994) Proc. Natl. Acad. Sci. USA 91:6496–6500; Semenza et al. (1994) J. Biol. Chem. 269:23757–23763).

The molecular mechanisms that mediate genetic responses to hypoxia have been extensively investigated for the EPO gene, which encodes a growth factor that regulates erythropoiesis and therefore blood $O_2$-carrying capacity (Jelkmann (1992) supra; Semenza (1994) supra). Cis-acting DNA sequences required for transcriptional activation in response to hypoxia were identified in the EPO 3'-flanking region. A trans-acting factor that binds to this transcriptional activation region has been identified: hypoxia-inducible factor 1α (HIF-1α). Several lines of evidence indicate that HIF-1α is a physiological regulator of EPO transcription. Inducers of EPO expression, including 1% $O_2$, cobalt chloride, and desferrioxamine, induce HIF-1α DNA binding activity with similar kinetics. Moreover, inhibitors of EPO expression, including actinomycin D, cycloheximide, and 2-aminopurine, blocked induction of HIF-1α activity. Mutations in the EPO 3'-flanking region eliminate HIF-1α binding and HIF-1α transcriptional activation (Semenza (1994) supra).

Induction of HIF-1 activity by 1% $O_2$, $CoCl_2$, or desferrioxamine (DFX) has been detected in many mammalian cell lines (Wang & Semenza (1993a) Proc. Natl. Acad. Sci. USA 90:4304–4308). Reporter genes linked to the EPO enhancer and transfected into non-EPO-producing cells were actively transcribed by hypoxia-inducible factor (Wang & Semenza (1993a) supra; Maxwell et al. (1993) Proc. Natl. Acad. Sci. USA 90:2423–2427). RNAs encoding several glycolytic enzymes were induced by 1% $O_2$, $CoCl_2$, or DFX in EPO-producing Hep3B or non-producing HeLa cells. However, cycloheximide blocked such induction. Moreover, glycolytic gene sequences containing HIF-1 binding sites exhibited hypoxia-inducible transcription in transfection assays (Firth et al. (1994) supra; Semenza et al. (1994) supra). These experiments support the role of HIF-1 in activating homeostatic responses to hypoxia.

Angiogenesis, or the process of producing new blood vessels in the body, is a key step in a number of biological responses to injury, stroke, or sudden loss of oxygen. In most cells this process is under tight control by a series of oxygen-sensitive proteins that act in concert to prevent undue blood vessel formation. A key protein mediator of this response is vascular endothelial growth factor (VEGF), a potent stimulator of blood vessel growth. Tumor cells often express this protein at levels 3–10 times higher than normal cells. Consequently, much attention has been directed at developing anticancer strategies focused on inhibiting the action of VEGF.

However, despite its positive role in healing injured tissues and in responding to hypoxia, little or no attention has been placed on stimulating the body to produce more VEGF. Instead, most research has been targeted on providing anti-angiogenic approaches for use in cancer treatment. There are a number of diseases, conditions and injuries that would benefit from VEGF activation. Accordingly, a need exists for factors that can stimulate VEGF production.

SUMMARY OF THE INVENTION

The invention provides peptides that can inhibit ubiquitination of hypoxia-inducible factor 1 alpha and activate transcription of EPO, VEGF and certain glycolytic enzymes. In one embodiment, the peptide has an amino acid sequence with at least 90% identity to SEQ ID NO:4, SEQ ID NO:5 or SEQ ID NO:7. Desirable peptides have an amino acid sequence comprising SEQ ID NO:4, SEQ ID NO:5 or SEQ ID NO:7.

The invention therefore provides an inhibitor of hypoxia-inducible factor 1 alpha ubiquitination comprising a peptide of formula I or II:

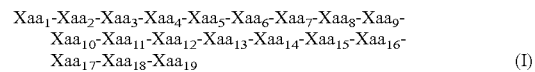

wherein $Xaa_1$, $Xaa_3$, $Xaa_5$, $Xaa_{14}$, $Xaa_{15}$ and $Xaa_{16}$ are each a separate acidic amino acid;

$Xaa_2$, $Xaa_4$, $Xaa_7$, $Xaa_8$, $Xaa_{11}$ and $Xaa_{19}$ are each a separate aliphatic amino acids;

$Xaa_6$, $Xaa_{10}$ and $Xaa_{18}$ are each a separate polar amino acid;

$Xaa_9$ is hydroxyproline;

$Xaa_{12}$ and $Xaa_{13}$ are separately an apolar amino acid such as methionine, glycine or proline; and $Xaa_{17}$ is an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine.

Acidic amino acids include, for example, aspartic acid or glutamic acid. Aliphatic amino acids include, for example, alanine, valine, leucine, isoleucine, n-butylalanine, t-butylalanine, N-methylisoleucine, norleucine, N-methylvaline, cyclohexylalanine, β-alanine, N-methylglycine, or α-aminoisobutyric acid. Polar amino acids include, for example, asparagine, glutamine, serine, threonine, tyrosine, citrulline, N-acetyl lysine, methionine sulfoxide, or homoserine. Apolar amino acids include, for example, methionine, glycine or proline. Aromatic amino acids include, for example, phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine.

In another embodiment, the invention provides an activator of EPO, VEGF or glycolytic enzyme transcription comprising a peptide of formula I or II, as provided above.

The invention further provides pharmaceutical compositions comprising a peptide of formula I or II and a pharmaceutically acceptable carrier. Such compositions can be sustained release formulations, and/or be used in conjunction with surgical implants, wound dressings and the like.

The invention also provides methods for inhibiting ubiquitination of hypoxia-inducible factor 1 alpha in a mammalian cell that involve contacting a peptide of formula I or II to a mammalian cell. In another embodiment, the invention provides methods for inhibiting ubiquitination of hypoxia-inducible factor 1 alpha in a mammal that involve administering therapeutically effective amount of a peptide of formula I or II to the mammal. Such administration can be localized to a site of tissue injury, for example, to a portion of the heart damaged by ischemia or to neural tissue injured by stroke.

The invention further provides methods for activating transcription EPO, VEGF or glycolytic enzymes in a mammalian cell that involve contacting a peptide of formula I or II to the mammalian cell. In another embodiment, the invention provides methods for activating transcription EPO, VEGF or glycolytic enzymes in a mammal that involve administering therapeutically effective amount of a peptide of formula I or II to the mammal. Such administration can be localized to a site of tissue injury, for example, to a portion of the heart damaged by ischemia or to neural tissue injured by stroke. In a desirable embodiment, VEGF transcription is activated.

DETAILED DESCRIPTION OF THE INVENTION

The invention relates to methods and compositions for activating VEGF, EPO and/or glycolytic enzyme transcription by inhibiting ubiquitination of hypoxia-inducible factor-1α. Such methods and compositions are useful for a variety of therapeutic purposes. For example, the compositions and methods of the invention can be used to treat tissue injuries including wounds, surgical incisions, chronic wounds, heart disease, stroke, and the like.

Hypoxia-inducible Factor-1

Hypoxia-inducible factor-1 (HIF-1) is a DNA-binding protein that binds to transcription regulatory sites such as the promoters and enhancers of several structural genes. Structural genes that can be activated by HIF-1 encode proteins such as erythropoietin (EPO), vascular endothelial growth factor (VEGF), and glycolytic enzymes. Such activation occurs in cells subjected to hypoxia.

Analysis of purified HIF-1 shows that it is composed of HIF-1α and HIF-1β subunits, where HIF-1β is an isoform of HIF-1α. In addition to having domains that allow for their mutual association in forming HIF-1, the HIF-1α and HIF-1β subunits of HIF-1 both contain DNA-binding domains. The alpha subunit is uniquely present in HIF-1, whereas the beta subunit is a component of at least two other transcription factors.

A sequence for hypoxia-inducible factor 1 alpha (SEQ ID NO:1 is provided below.

```
  1 MEGAGGANDK  KKISSERRKE  KSRDAAPSRR  SKESEVFYEL  AHQLPLPHNV

51 SSHLDKASVM  RLTISYLRVR  KLLDAGDLDI  EDDMKAQMNC  FYLKALDGFV

101 MVLTDPGDMI  YISDNVNKYM  GLTQFELTGH  SVFDFTHPCD  HEEMREMLTH

151 RNGLVKKGKE  QNTQRSFFLR  MKCTLTSRGR  TMNIKSATWK  VLHCTGHTHV

201 YDTNSNQPQC  GYKKPPMTCL  VLICEPIPHP  SNIEIPLDSK  TFLSRHSLDM

251 KFSYCDERIT  ELMGYEPEEL  LGRSIYEYYH  ALDSDHLTKT  HHDMFTKGQV

301 TTGQYRMLAK  RGGYVWVETQ  ATVIYNTKNS  QPQCIVCVNY  VVSGIIQHDL

351 IFSLQQTECV  LKPVESSDMK  MTQLFTKVES  EDTSSLFDKL  KKEPDALTLL

401 APAAGDTIIS  LDFGSNDTET  DDQQLEEVPL  YNDVMLPSPN  EKLQNINLAM

451 SPLPTAETPK  PLRSSADPAL  NQEVALKLEP  NPESLELSFT  MPQIQDQTPS

501 PSDGSTRQSS  PEPNSPSEYC  FYVDSDMVNE  FKLELVEKLF  AEDTEAKNPF

551 STQDTDLDLE  MLAPYIPMDD  DFQLRSFDQL  SPLESSSASP  ESASPQSTVT

601 VFQQTQIQEP  TANATTTTAT  TDELKTVTKD  RMEDIKILIA  SPSPTHIHKE

651 TTSATSSPYR  DTQSRTASPN  RAGKGVIEQT  EKSHPRSPNV  LSVALSQRTT

701 VPEEELNPKI  LALQNAQRKR  KMEHDGSLFQ  AVGIGTLLQQ  PDDHAATTSL

751 SWKRVKGCKS  SEQNGMEQKT  IILIPSDLAC  RLLGQSMDES  GLPQLTSYDC

801 EVNAPIQGSR  NLLQGEELLR  ALDQVN
```

A sequence for a variant of hypoxia-inducible factor-1 alpha (SEQ ID NO:2) is also provided below.

```
  1 MEGAGGANDK  KKISSERRKE  KSRDAARSRR  SKESEVFYEL  AHQLPLPHNV
 51 SSHLDKASVM  RLTISYLRVR  KLLDAGDLDI  EDDMKAQMNC  FYLKALDGFV
101 MVLTDDGDMI  YISDNVNKYM  GLTQFELTGH  SVFDFTHPCD  HEEMREMLTH
151 RNGLVKKGKE  QNTQRSFFLR  MKCTLTSRGR  TMNIKSATWK  VLHCTGHIHV
201 YDTNSNQPQC  GYKKPPMTCL  VLICEPIPHP  SNIEIPLDSK  TFLSRHSLDM
251 KFSYCDERIT  ELMGYEPEEL  LGRSIYEYYH  ALDSDHLTKT  HHDMFTKGQV
301 TTGQYRMLAK  RGGYVWVETQ  ATVIYNTKNS  QPQCIVCVNY  VVSGIIQHDL
351 IFSLQQTECV  LKPVESSDMK  MTQLFTKVES  EDTSSLFDKL  KKEPDALTLL
401 APAAGDTIIS  LDFGSNDTET  DDQQLEEVPL  YNDVMLPSPN  EKLQNINLAM
451 SPLPTAETPK  PLRSSADPAL  NQEVALKLEP  NPESLELSFT  MPQIQDQTPS
501 PSDGSTRQSS  PEPNSPSEYC  FYVDSDMVNE  FKLELVEKLF  AEDTEAKNPF
551 STQDTDLDLE  MLAPYIPMDD  DFQLRSFDQL  SPLESSSASP  ESASPQSTVT
601 VFQQTQIQEP  TANATTTTAT  TDELKTVTKD  RMEDIKILIA  SPSPTHIHKE
651 TTSATSSPYR  DTQSRTASPN  RAGKGVIEQT  EKSHPRSPNV  LSVALSQRTT
701 VPEEELNPKI  LALQNAQRKR  KMEHDGSLFQ  AVGII
```

A sequence for hypoxia-inducible factor 1 beta (SEQ ID NO:3) is provided below.

```
  1 MAATTANPEM  TSDVPSLGPA  IASGNSGPGI  QGGGAIVQRA  IKRRPGLDFD
 51 DDGEGNSKFL  RCDDDQMSND  KERFARSDDE  QSSADKERLA  RENHSEIERR
101 RRNKMTAYIT  ELSDMVPTCS  ALARKPDKLT  ILRMAVSHMK  SLRGTGNTST
151 DGSYKPSFLT  DQELKHLILE  AADGFLFIVS  CETGRVVYVS  DSVTPVLNQP
201 QSEWFGSTLY  DQVHPDDVDK  LREQLSTSEN  ALTGRILDLK  TGTVKKEGQQ
251 SSMRMCMGSR  RSFICRMRCG  SSSVDPVSVN  RLSFVRNRCR  NGLGSVKDGE
301 PHFVVVHCTG  YIKAWPPAGV  SLPDDDPEAG  QGSKFCLVAI  GRLQVTSSPN
351 CTDMSNVCQP  TEFISRHNIE  GIFTFVDHRC  VATVGYQPQE  LLGKNIVEFC
401 HPEDQQLLRD  SFQQVVKLKG  QVLSVMFRFR  SKNQEWLWMR  TSSFTFQNPY
451 SDEIEYIICT  NTNVKNSSQE  PRPTLSNTIQ  RPQLGPTANL  PLEMGSGQLA
501 PRQQQQQTEL  DMVPGRDGLA  SYNHSQVVQP  VTTTGPEHSK  PLEKSDGLFA
551 QDRDPRFSEI  YHNINADQSK  GISSSTVPAT  QQLFSQGNTF  PPTPRPAENF
601 RNSGLAPPVT  IVQPSASAGQ  MLAQISRHSN  PTQGATPTWT  PTTRSGFSAQ
651 QVATQATAKT  RTSQFGVGSF  QTPSSFSSMS  LPGAPTASPG  AAAYPSLTNR
701 GSNFAPETGQ  TAGQFQTRTA  EGVGVWPQWQ  GQQPHHRSSS  SEQHVQQPPA
751 QQPGQPEVFQ  EMLSMLGDQS  NSYNNEEFPD  LTMFPPFSE
```

The steady-state concentration of HIF-1α is tightly controlled by a complex between the von Hippel Lindau protein, Elongin B and Elongin C (the "VBC" complex) under conditions of normal oxygenation. The VBC complex binds and targets HIF-1α for polyubiquitination and destruction. However, this complex binds only to hydroxylated HIF-1α.

A proline at about position 564 of hypoxia-inducible factor-1 alpha is hydroxylated by a prolyl hydroxylase in a reaction requiring molecular oxygen and iron ($Fe^{+2}$). This reaction takes place efficiently when normal levels of oxygen and iron are available. As a result, almost all HIF-1α is hydroxylated in normally oxygenated cells. The VBC complex binds only to hydroxylated HIF-1α. Hence, when normal levels of oxygen and iron are present, proline 564 in HIF-1α is hydroxylated, the VBC complex ubiquitinates the hydroxylated HIF-1α and HIF-1α is destroyed.

However, under conditions of low oxygen or of iron depletion, the proline 564 of HIF-1α is not hydroxylated, and HIF-1α rapidly accumulates in the cells. Under these conditions, HIF-1α is available to activate the transcription of a number of factors, including erythropoietin (EPO), vascular endothelial growth factor (VEGF) and certain glycolytic enzymes.

Peptide Inhibitors

According to the present invention, peptides having sequences related to an oxygen-dependent degradation domain (ODD) of hypoxia-inducible factor-1 alpha will inhibit the ubiquitination of hypoxia-inducible factor-1 alpha and prolong the half-life of this protein in vivo. The invention provides peptides having sequences related to the hypoxia-inducible factor-1 alpha ODD that will increase transcription of erythropoietin (EPO), vascular endothelial growth factor (VEGF) and/or glycolytic enzymes. Also, according to the present invention, peptides having sequences related to the hypoxia-inducible factor-1 alpha ODD domain will promote angiogenesis.

The ODD domain of hypoxia-inducible factor-1 alpha is a polypeptide segment comprising amino acids ranging from approximately 555 to approximately 575 that contains the proline that can be hydroxylated to permit interaction with the VBC complex. Peptides with sequences related to the hypoxia-inducible factor-1 alpha ODD are contemplated by the invention, as well as variant peptides that have one or more amino acids substituted for the amino acids that are naturally present in hypoxia-inducible factor-1 alpha polypeptides. Mixtures of ODD-related peptides with different sequences are also contemplated. In general, the ODD-related peptides, peptide variants and mixtures of peptides are formulated and used in a manner that optimally enhances EPO, VEGF or glycolytic enzyme transcription. In another embodiment, the peptide sequences, peptide variants and mixtures of peptides are formulated and used in a manner that optimally inhibits ubiquitination of hypoxia-inducible factor-1 alpha. Hence, the composition and formulations of the present peptides can be varied so that lesser or greater levels of inhibition are achieved so long as hypoxia-inducible factor-1 alpha ubiquitination is inhibited, or EPO, VEGF or glycolytic enzyme transcription is activated, or angiogenesis and/or healing is promoted at the site where the peptide inhibitors are administered.

The size of a peptide inhibitor can vary. In general, a peptide of only about four amino acids can be too small to provide optimal inhibition. However, peptides of more than about five to six amino acids may be sufficiently long to provide inhibition. Therefore, while the overall length is not critical, peptides longer than about five amino acids are desired. More desirable peptides are longer than about six amino acids. Even more desirable peptides are longer than about seven amino acids. Even more desirable peptides are longer than about eight amino acids. Especially desired peptides are longer than about eight amino acids.

There is no particular upper limit on peptide size. However, it is generally cheaper to make shorter peptides than longer peptides. Moreover, small peptides may diffuse and travel through membranes better. Hence, the peptide inhibitors of the invention are generally shorter than about one hundred amino acids. Desirable peptide inhibitors are shorter than seventy five amino acids. More desirable peptide inhibitors are shorter than about fifty amino acids. Even more desirable peptides are shorter than about forty-five amino acids. Especially desirable peptides are shorter than about forty amino acids. Examples of desirable peptides include those with sequences related to SEQ ID NO:4 with eight amino acids, and SEQ ID NO:5 with nineteen amino acids.

| | |
|---|---|
| MLA(Hyp)TIPM | (SEQ ID NO:4) |
| DLDLEMLA(Hyp)YIPMDDDFQL | (SEQ ID NO:5) |

In the above sequences, (Hyp) indicates hydroxyproline.

Peptide inhibitors contemplated by the invention include peptide derivatives and variants of a peptide having any one of SEQ ID NO:4 or 5. Such peptide derivatives and variants can have one or more amino acid substitutions, deletions, insertions or other modifications so long as the peptide variant can inhibit hypoxia-inducible factor-1 alpha ubiquitination, or activate EPO, VEGF or glycolytic enzyme transcription, or promote angiogenesis and/or healing at the site where the peptide variants are administered.

In one embodiment the derivative peptide can have an eleven-amino acid sequence (YGRKKRRQRRR, SEQ ID NO:6) that has been shown to rapidly facilitate transport of numerous peptides and proteins across the cell wall and into the cytoplasm (see Schwarze et al. Science, 285, 1569 (1999)). In a further embodiment, peptides having sequences related to YGRKKRRQRRR-DLDLEMLA(Hyp) YIPMD-DDFQL (SEQ ID NO:7) are contemplated as peptide inhibitors of the invention.

Amino acid residues of the isolated peptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Hydroxyproline | | Hyp |
| β-Alanine | | BAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |

TABLE 1-continued

| Amino Acid | One-Letter Symbol | Common Abbreviation |
| --- | --- | --- |
| Naphthylalanine | | Nal |
| Pyridylananine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | HArg |
| N-acetyl lysine | | AcLys |
| 2,4-Diamino butyric acid | | Dbu |
| p-Aminophenylalanine | | Phe(pNH$_2$) |
| N-methylvaline | | MeVal |
| Homocysteine | | HCys |
| Homoserine | | Hser |
| ε-Amino hexanoic acid | | Aha |
| δ-Amino valeric acid | | Ava |
| 2,3-Diaminobutyric acid | | Dab |

Peptides that are encompassed within the scope of the invention can have one or more amino acids substituted with an amino acid of similar chemical and/or physical properties, so long as these variant peptides retain the ability to inhibit hypoxia-inducible factor-1 alpha ubiquitination, or activate EPO, VEGF or glycolytic enzyme transcription, or promote angiogenesis and/or healing at the site where the peptide variants are administered.

Amino acids that are substitutable for each other generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded and which can be present, or substituted for an amino acid, in the peptides and peptide analogues of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit);

t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the peptides and peptide variants and derivatives described herein. Other amino acid residues that are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Hydrophobic | I, L, V | t-BuA |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | S, K | Cit , hCys. |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Peptides of the invention can have any amino acid substituted by any similarly classified amino acid to create a variant peptide, so long as the peptide variant retains an ability to inhibit hypoxia-inducible factor-1 alpha ubiquitination, or activate EPO, VEGF or glycolytic enzyme transcription, or promote angiogenesis and/or healing at the site where the peptide variants are administered.

In one embodiment, the peptide inhibitors of the invention include any one of peptide formulae I or II.

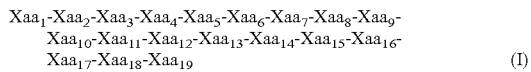

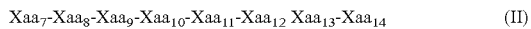

wherein

Xaa$_1$, Xaa$_3$, Xaa$_5$, Xaa$_{14}$, Xaa$_{15}$ and Xaa$_{16}$ are separate acidic amino acids, for example, aspartic acid or glutamic acid;

Xaa$_2$, Xaa$_4$, Xaa$_7$, Xaa$_8$, Xaa$_{11}$ and Xaa$_{19}$ are separate aliphatic amino acids such as alanine, valine, leucine, isoleucine, t-butylalanine, t-butylalanine, -methylisoleucine, norleucine, N-methylvaline, cyclohexylalanine, β-alanine, N-methylglycine, or α-aminoisobutyric acid;

Xaa$_6$ and Xaa$_{18}$ are separate polar amino acids, for example, asparagine, glutamine, serine, threonine, tyrosine, citrulline, N-acetyl lysine, methionine sulfoxide, or homoserine;

Xaa$_9$ is hydroxyproline;

Xaa$_{10}$ is a polar amino acid, for example, a polar amino acid such as asparagine, glutamine, serine, threonine, tyrosine, citrulline, N-acetyl lysine, methionine sulfoxide, or homoserine, Xaa$_{12}$ and Xaa$_{13}$ are separately an apolar amino acid such as methionine, glycine or proline; and Xaa$_{17}$ is an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine.

In a desirable embodiment:
Xaa$_1$ is aspartic acid,
Xaa$_2$ is leucine,
Xaa$_3$ is aspartic acid,
Xaa$_4$ is leucine,
Xaa$_5$ is glutamic acid,
Xaa$_6$ is methionine,
Xaa$_7$ is leucine,
Xaa$_8$ is alanine,
Xaa$_9$ is hydroxyproline,
Xaa$_{10}$ is tyrosine,
Xaa$_{11}$ is isoleucine,
Xaa$_{12}$ is proline,
Xaa$_{13}$ is methionine,
Xaa$_{14}$ is aspartic acid,
Xaa$_{15}$ is aspartic acid,
Xaa$_{16}$ is aspartic acid,
Xaa$_{17}$ is phenylalanine,
Xaa$_{18}$ is glutamine, and
Xaa$_{19}$ is leucine.

Desirable peptides of the invention also include the sequences defined by SEQ ID NO:4, 5 and 7. A nineteen amino acid peptide having SEQ ID NO:5 and a thirty amino acid peptide having SEQ ID NO:7 are particularly desirable. Peptides having SEQ ID NO:5 or 7 have a segment related to the hydroxylation site hypoxia-inducible factor-1 alpha, efficiently inhibit ubiquitination of hypoxia-inducible factor-1 alpha and activate transcription of EPO, VEGF and certain glycolytic enzymes several-fold. Peptides having SEQ ID NO:7 also have an eleven-amino acid sequence (YGRKKRRQRRR, SEQ ID NO:6) that has been shown to rapidly facilitate transport of numerous peptides and proteins across the cell wall and into the cytoplasm (reference: Schwarze et al. Science, 285, 1569 (1999)).

A single peptide having a sequence related to that of SEQ ID NO:5 or 7 can be used to inhibit hypoxia-inducible factor-1 alpha ubiquitination, or activate EPO, VEGF or glycolytic enzyme transcription, or promote angiogenesis and/or healing at the site where the peptide variants are administered. A formulation of such a single peptide may provide partial or substantially complete inhibition of ubiquitination and/or transcriptional activation of EPO, VEGF or glycolytic enzymes. Partial inhibition of ubiquitination and/or transcriptional activation of EPO, VEGF or glycolytic enzymes may facilitate angiogenesis or healing. Alternatively, two or more peptides can be combined to provide even more complete inhibition of ubiquitination and/or transcriptional activation of EPO, VEGF or glycolytic enzymes. One of skill in the art can therefore design an appropriate peptide inhibitor or combination of peptide inhibitors to achieve the quantity of inhibition desired using available teachings in combination with the teachings provided herein. One of skill in the art can readily make modifications to the peptides provided by the invention and observe the degree to which ubiquitination is inhibited and/or transcription of EPO, VEGF or glycolytic enzymes is activated.

Peptide Modifications

The invention also contemplates modifying the peptide inhibitors to stabilize them, to facilitate their uptake and absorption and to improve any other characteristic or property of the peptides that is known to one of skill in art. For example, the peptide inhibitors can be joined to other peptides, cyclized, charges on the peptide inhibitors can be neutralized, and the peptides can be linked to other chemical moieties.

Peptides can be cyclized by any method available to one of skill in the art. For example, the N-terminal and C-terminal ends can be condensed to form a peptide bond by known procedures. Functional groups present on the side chains of amino acids in the peptides can also be joined to cyclize the peptides of the invention. For example, functional groups that can form covalent bonds include —COOH and —OH; —COOH and —NH$_2$; and —COOH and —SH. Pairs of amino acids that can be used to cyclize a peptide include, Asp and Lys; Glu and Lys; Asp and Arg; Glu and Arg; Asp and Ser; Glu and Ser; Asp and Thr; Glu and Thr; Asp and Cys; and Glu and Cys. Other examples of amino acid residues that are capable of forming covalent linkages with one another include cysteine-like amino acids such Cys, hCys, β-methyl-Cys and Pen, which can form disulfide bridges with one another. Desirable cysteine-like amino acid residues include Cys and Pen. Other pairs of amino acids that can be used for cyclization of the peptide will be apparent to those skilled in the art.

The groups used to cyclize a peptide need not be amino acids. Examples of functional groups capable of forming a covalent linkage with the amino terminus of a peptide include carboxylic acids and esters. Examples of functional groups capable of forming a covalent linkage with the carboxyl terminus of a peptide include —OH, —SH, —NH$_2$ and —NHR where R is (C$_1$–C$_6$) alkyl, (C$_1$–C$_6$) alkenyl and (C$_1$–C$_6$) alkynyl.

The variety of reactions between two side chains with functional groups suitable for forming such interlinkages, as well as reaction conditions suitable for forming such interlinkages, will be apparent to those of skill in the art. Preferably, the reaction conditions used to cyclize the peptides are sufficiently mild so as not to degrade or otherwise damage the peptide. Suitable groups for protecting the various functionalities as necessary are available in the art (see, e.g., Greene & Wuts, 1991, 2nd ed., John Wiley & Sons, NY), as are various reaction schemes for preparing such protected molecules.

In one embodiment the charges at the N-terminal and C-terminal ends are effectively removed. This can be done by any method available to one of skill in the art, for example, by acetylating the N-terminus and amidating the C-terminus.

Methods for preparing cyclic peptides and modifying peptide in other ways are available in the art (see, e.g., Spatola, 1983, Vega Data 1(3) for a general review); Spatola, 1983, "Peptide Backbone Modifications" In: Chemistry and Biochemistry of Amino Acids Peptides and Proteins (Weinstein, ed.), Marcel Dekker, New York, p. 267 (general review); Morley, 1980, Trends Pharm. Sci. 1:463–468; Hudson et al., 1979, Int. J. Prot. Res. 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH=CH—, cis and trans); Almquist et al., 1980, J. Med. Chem. 23:1392–1398 (—COCH$_2$—); Jennings-White et al., Tetrahedron. Lett. 23:2533 (—COCH$_2$—); European Patent Application EP 45665 (1982) CA:97:39405 (—CH(OH)CH$_2$—); Holladay et al., 1983, Tetrahedron Lett. 24:4401–4404 (—C(OH)CH$_2$—); and Hruby, 1982, Life Sci. 31:189–199 (—CH$_2$—S—).

Therapeutic Methods

Peptides of the invention can be for therapeutic purposes in diseases or injuries where insufficient blood flow has caused or may cause tissue damage (e.g., stroke, ischemia, chronic wounds). Individual peptides, peptide variants and mixtures of peptides with different sequences can be combined in a formulation to promote angiogenesis and healing of injured tissues.

Optimal therapeutic benefits may be achieved by permitting some ubiquitination of hypoxia-inducible factor-1 alpha. Hence, the compositions and formulations of the present invention do not necessarily promote maximal inhibition of hypoxia-inducible factor-1 alpha ubiquitination, or maximal activation of EPO, VEGF or glycolytic enzyme transcription, or maximal angiogenesis. Instead, the activity of the peptide inhibitor formulation is varied to optimize healing and prevent side effects. Lesser or greater levels of ubiquitination inhibition can be achieved by varying the type, content and amount of inhibitor peptides so that the therapeutic benefits are optimized and healing is promoted.

Moreover, one of skill in the art may choose to use a peptide formulation having maximal inhibition of hypoxia-inducible factor-1 alpha ubiquitination, or maximal activation of EPO, VEGF or glycolytic enzyme transcription, or maximal angiogenesis in a localized area. For example, one of skill in the art may directly apply such a formulation to a wound, or to heart tissues injured by heart disease, ischemia or progressive heart failure, or to neural tissues damaged by stroke. Alternatively, one of skill in the art may choose to use a peptide formulation having less than maximal inhibition of hypoxia-inducible factor-1 alpha ubiquitination, or less than maximal activation of EPO, VEGF or glycolytic enzyme transcription, or less than maximal angiogenesis in a non-localized area.

To treat injured heart, neural or other tissues, peptides of the invention can be introduced into the localized area of the injury in any manner chosen by one of skill in the art. For example, peptides can be formulated into a therapeutic composition containing a therapeutically effective amount of one or more peptides and a pharmaceutical carrier. Such a composition can be introduced into or onto the tissue as a cream, spray, foam, gel or in the form of any other formulation. In one embodiment, the peptide formulations of the invention are introduced into injured tissues as a coating on a surgical implant (e.g. a stent) or within a sustained delivery device.

In another embodiment, peptides of the invention can be formulated into a dressing for a wound containing a therapeutically effective amount of one or more peptides applied to, impregnated into, covalently attached or otherwise associated with, a dressing material. In one embodiment, the dressing permits immediate or sustained release of the peptide inhibitor. Release of the peptide inhibitor can be in an uncontrolled or a controlled manner. Hence, the wound dressings of the invention can provide slow or timed release of the peptide inhibitor into a wound. Dressing materials can be any material used in the art including bandage, gauze, sterile wrapping, hydrogel, hydrocolloid and similar materials.

A therapeutically effective amount of a peptide of the invention is an amount of peptide that inhibits ubiquitination or activates EPO, VEGF or glycolytic enzyme transcription to a degree needed to optimally treat injuries, diseases or conditions involving tissue damage from insufficient blood flow (e.g., stroke, ischemia, chronic wounds). Such a therapeutically effective amount of a peptide can inhibit ubiquitination or activate EPO, VEGF or glycolytic enzyme transcription to a degree needed to promote healing or angiogenesis.

For example, when present in a therapeutic or pharmaceutical composition, the amount of peptides of the invention can be in the range of about 0.1% to about 35% by weight of the composition. Preferably, the peptides form about 0.5% to about 20% by weight of the composition. More preferably, the peptides form about 1.0% to about 10% by weight of the composition.

The therapeutically effective amount of peptide inhibitor necessarily varies with the route of administration. For example, a therapeutic amount between 30 to 112,000 µg per kg of body weight can be effective for intravenous administration. However, the amount of the peptide inhibitor required for treatment of tissue injuries will vary not only with the route of administration, but also the nature of the condition being treated and the age and condition of the patient and will be ultimately at the discretion of the attendant physician or clinician.

The dosage and method of administration can vary depending on the location and severity of the tissue injury. Useful dosages of the present peptides can be determined by observing their in vitro activity or, preferably, their in vivo activity in animal models.

The peptides can conveniently be administered in unit dosage form; for example, in a unit dosage form containing about 0.001 µg to about 10 mg, conveniently about 0.01 µg to about 5 mg, more conveniently, about 0.10 µg to about 1 mg, and even more conveniently about 1.0 µg to 500 µg of peptide per unit dosage form. The desired dose may be presented in a single dose, as divided doses, or as a continuous infusion. The desired dose can also be administered at appropriate intervals, for example, as two, three, four or more sub-doses per day. One of skill in the art can readily prepare and administer an effective formulation from available information using the teachings provided herein.

The peptide inhibitors of the invention can be formulated as pharmaceutical compositions and administered to a mammalian host, such as a human patient in a variety of dosage forms adapted to the chosen route of administration, i.e., topically, orally, parenterally, intravenously, intramuscularly, subcutaneously or by surgical implant.

Thus, the peptide inhibitors may be systemically administered, for example, intravenously or intraperitoneally by infusion or injection. Solutions of the peptide inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the peptide or peptide conjugate in the required amount in the appropriate solvent with various of the other ingredients enumerated above, as required, followed by filter sterilization. In the case of sterile powders for the preparation of sterile injectable solutions, desirable methods of preparation are vacuum drying and the freeze drying techniques, which yield a powder of the active ingredient plus any additional desired ingredient present in the previously sterile-filtered solutions.

In some instances, the peptide inhibitors can also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the peptide inhibitor may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptide inhibitor may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In general, the peptides of the invention are preferably administered topically for treatment of tissue injuries or by surgical implant of internal tissue injuries (e.g. heart tissue and neural tissue injuries).

The active peptides may be administered topically by any means either directly or indirectly to the affected tissue as sprays, foams, powders, creams, jellies, pastes, suppositories or solutions. The term paste used in this document should be taken to include creams and other viscous spreadable compositions such as are often applied directly to the skin or spread onto a bandage or dressing. Peptides of the invention can be covalently attached, stably adsorbed or otherwise applied to a wound dressing material. The compositions can be administered by aerosol, as a foam or as a mist along with other agents directly onto the wound.

To facilitate healing after internal tissue injury (e.g. ischemia or stroke) or after surgery, the active peptides of the invention can be applied directly to target tissues, or administered within a surgical implant or prosthetic device. The peptides can be administered in a formulation that can include an emulsion of the peptide in a wax, oil, an emulsifier, water, water-soluble polymer and/or a substantially water-insoluble material that forms a gel in the presence of water.

A formulation containing the present peptides can provide the desirable properties of an emulsion or cream that it is spreadable and has the creamy consistency of an emulsion. Such a formulation does not break down when subjected to normal sterilization procedures, e.g. steam sterilization, because stabilizers are present in the emulsion.

The formulation can contain a humectant to reduce the partial vapor pressure of the water in a creamy formulation to reduce the rate at which the cream dries out. Suitable humectants are preferably not solvents for a gel-forming material, but are generally miscible with water and are preferably suitable for application to the skin. Polyols are especially suitable for the purpose and suitable polyols may include monopropylene glycol or glycerine (glycerol). The polyol may be present in proportions of 20–50% (by weight) of the total formulation; a desirable range is 30–40%. This relatively high proportion of polyol also ensures that if the paste should dry out to any degree, the resulting paste remains soft and flexible because the glycerin may act as a plasticiser for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

The formulation can include other ingredients. Ingredients which may be used include: zinc oxide, ichthammol, calamine, silver suphadiazine, chlorhexidine acetate, coal tar, chlorhexidine gluconate, metronidazole or other antibacterial agents, or a combination thereof. Other ingredients may also be found suitable for incorporation into the cream.

These ingredients can be included in beneficial amounts, for example, up to about 15 wt %, of zinc oxide may be added; typically 6–10% of zinc oxide is used, possibly in combination with another ingredient such as ichthammol (0–3 wt %) and/or calamine (0–15 wt %). Ichthammol or calamine may also be used alone. Chlorhexidine acetate can be used at a concentration of up to 1% by weight; 0.5 wt % is typical.

A suggested wax for the emulsion is glyceryl monostearate, or a combination of glyceryl monostearate and PEG100 stearate which is available commercially as CITHROL GMS/AS/NA from Croda Universal Ltd. This combination provides both a wax and an emulsifier (PEG 100 stearate) which is especially compatible with the wax, for forming an emulsion in water. A second emulsifier can be included in the formulation to increase the stability of the emulsion, for example, a PEG20 stearate, such as CITHROL 1OMS which is supplied by Croda Universal Ltd. The total concentration of emulsifier in the cream should normally be in the range of from 3–15%. Where two emulsifiers are used, one may be present in a greater concentration than the other.

A water-insoluble material that forms a gel with the water of the formulation can also be used with the peptides of the invention. Such a material is selected to be hydrophilic but not to dissolve in water to any great extent. The material is most preferably a polymeric material that is a water-absorbing non-water-soluble polymer. However, non-polymeric materials that form gels with water and that are stable at elevated temperatures could also be used, e.g. clays such as kaolin or bentonite.

Desirable polymers are super-absorbent polymers such as those disclosed in WO-92/16245 and that comprise hydrophilic cellulose derivatives which have been partially cross-linked to form a three dimensional structure. Suitable cross-linked cellulose derivatives include those of the hydroxy lower alkyl celluloses, wherein the alkyl group contains from 1 to 6 carbon atoms, e.g. hydroxyethyl cellulose or hydroxypropyl-cellulose, or the carboxy-celluloses e.g. carboxymethyl hydroxyethyl cellulose or carboxymethylcellulose. A particularly desirable polymer is a partially cross-linked sodium carboxymethylcellulose supplied as AKUCELL X181 by Akzo Chemicals B.V. This polymer is a superabsorbent polymer in that it may absorb at least ten times its own weight of water. The cross-linked structure of the polymer prevents it from dissolving in water but water is easily absorbed into and held within the three-dimensional structure of the polymer to form a gel. Water is lost less rapidly from such a gel than from a solution and this is advantageous in slowing or preventing the drying out of the cream formulation. The polymer content of the formulation is normally less than 10%, preferably in the range from 0.5–5.0% by weight, and, in desirable formulations, usually will be between 1.0% and 2%.

The formulation may be sterilized and components of the formulation should be selected, by varying the polymer content, to provide the desired flow properties of the finished product. That is, if the product is intended to be sterilized, then the formulation should be chosen to give a product of relatively high viscosity/elasticity before sterilization. If certain components of the formulation are not intended to be sterilized, the formulation can be sterilized before addition of those components, or each component can be sterilized separately. The formulation can then be made by mixing together each sterile, or sterilized, ingredient under sterile conditions. When components are separately sterilized and then mixed together, the polymer content can be adjusted to give a product having the desired flow properties of the finished product. The emulsion content determines the handling properties and feel of the formulation, higher emulsion content leading to increased spreadability and creaminess.

The formulation may be packaged into tubes, tubs, surgical implants, sustained delivery devices or other suitable containers for storage or it may be spread onto a substrate and then subsequently packaged. Suitable substrates include surgical implants and dressings, including film dressings, and bandages.

The following examples are intended to illustrate but not limit the invention.

EXAMPLE

ODD Peptide Inhibitor Upregulates Angiogenesis

In this example, a novel peptide-based reagent was used to interfere with the natural regulatory network that holds VEGF production in check. This strategy is based on two key observations—1) the oxygen-sensitive regulation of angiogenesis is controlled by ubiquitination and protease degradation of a single transcription factor (HIF-1α); and 2) such degradation is accomplished by a unique recognition between a ternary protein complex between von Hippel Lindau protein, Elongin B and Elongin C (VBC complex) and a highly conserved 19 amino acid sequence in HIF-1α that is hydroxylated at a key residue. According to the present invention this unique recognition event is interrupted by a peptide containing the same 19 amino acid sequence, key angiogenic genes (such as VEGF) are upregulated without significant impact on other biological pathways.

Materials and Methods

Peptide Synthesis. In order to test our hypothesis that angiogenesis could be stimulated by selective inhibition of the action of the VBC complex on HIF-1α, the following peptide having SEQ ID NO:7 (termed the "ODD peptide") was synthesized using standard FMOC chemistry and purified by reverse phase HPLC:

```
YGRKKRRQRRR-DLDLEMLA(Hyp)YIPMDDDFQL
(SEQ ID NO: 7)
```

This peptide contains two key domains: 1) the oxygen-dependent degradation sequence of HIF-1α (DLDLEMLA(Hyp)YIPMDDDFQL, SEQ ID NO:5), a 19 residue sequence that, upon hydroxylation of a key proline, is recognized by VBC and initiates that ubiquitination of the parent protein; and 2) an 11-amino acid sequence (YGRKKRRQRRR, SEQ ID NO:6) that has been shown to rapidly facilitate transport of numerous peptides and proteins across the cell wall and into the cytoplasm (reference: Schwarze et al. Science, 285, 1569 (1999)).

The goal was to readily transport a peptide having SEQ ID NO:7 into human cell types where it would act as a competitive inhibitor of VBC ubiquitination. The steady-state concentration of HIF-1α is tightly controlled by VBC under normoxic conditions, but under hypoxic conditions the proline 564 is not hydroxylated, and HIF-1α rapidly accumulates in the cells. It was believed that this peptide would allow for accumulation of HIF-1α even under normal oxygen conditions, leading to increased gene expression of key angiogenic gene products such as vascular endothelial growth factor (VEGF).

Treatment of Human Dermal Fibroblasts with ODD Peptide.

Neonatal human dermal fibroblasts (CC-2509 from Biowhittaker, Inc.) were grown in fibroblast growth media supplemented with 10% FBS and growth factors to approximately 80% confluency at 37° C., 5% $CO_2$. Media was replaced with fresh media (negative control), or media containing either 1 mg/mL ODD peptide (experiment) or 100 micromolar $CoCl_2$ (a positive control known to induce a hypoxic response). Cells were incubated at 37° C. in an atmosphere containing 5% $CO_2$ for 12 hr.

Isolation of Total RNA

Total RNA was isolated from treated cells using reagents and methods from Ambion (RNAeasy kit). Typical yields from a single T-25 flask of cells was 15–25 micrograms of total RNA.

Microarray Experiments

Three (3) ug of total RNA from each sample (negative control, positive ($CoCl_2$) control, and ODD-treated sample) were converted to labeled cDNA using the Genisphere 3DNA kit. cDNAs were labeled with either Cy3 or Cy5, and hybridized overnight at 37° C. onto microarrays containing over 700 unique human gene sequences (Stress and Aging OpArrays, Operon Technologies). Densitometric scanning of these arrays was used to quantify the relative amounts of gene expression between treated and untreated controls, and these data were normalized for small differences in detection sensitivity between the two dyes, and for possible differences in the amount of input RNA used.

Results

Densitometric comparison of gene expression levels between untreated and $CoCl_2$-treated or ODD peptide-treated fibroblasts revealed the following patterns in expression of key genes involved in angiogenesis and hypoxic response:

| Gene | $CoCl_2$-treated | ODD peptide-treated |
|---|---|---|
| VEGF A | up 3.4 x | up 3.2 x |
| VEGF B | up 1.4 x | up 1.4 x |
| VEGF C | up 3.0 x | up 4.4 x |

Each gene expression ratio was measured in triplicate, and the reported ratios are those of treated/untreated.

These data indicate that the ODD peptide is effectively transported into human cells, and inhibits the ubiquitination of HIF-1α. Transcription of all three common VEGF isoforms that are transcriptionally regulated by HIF-1α was upregulated by exposure of cells to the ODD peptide. These VEGF gene products are among the most potent angiogenesis stimulators known. Hence, use of the ODD peptide inhibitor can be used for therapeutic purposes in diseases or injuries where insufficient blood flow has caused or may cause tissue damage (e.g., stroke, ischemia, chronic wounds).

What is claimed:

1. An isolated peptide consisting of SEQ ID NO:7.

2. A pharmaceutical formulation comprising a pharmaceutically acceptable carrier and a peptide that consists of SEQ ID NO:7.

3. The pharmaceutical formulation of claim 2 that is administered in conjunction with a wound dressing.

4. The pharmaceutical formulation of claim 2 that is a sustained release formulation.

5. The pharmaceutical formulation of claim 2 that is administered in conjunction with a surgical implant.

* * * * *